(12) United States Patent
Kwon et al.

(10) Patent No.: US 8,318,662 B2
(45) Date of Patent: Nov. 27, 2012

(54) PROTEIN INCREASING CELL INFECTIVITY OF HERPES SIMPLEX VIRUS AND USE THEREOF

(75) Inventors: Hee Chung Kwon, Seoul (KR); Hyun Jung Baek, Seoul (KR); Kee Ho Lee, Seoul (KR); Masahide Kuroki, Fukuoka (JP)

(73) Assignee: Korea Institute of Radiological & Medical Sciences (KR)

( * ) Notice: Subject to any disclaimer, the term of this patent is extended or adjusted under 35 U.S.C. 154(b) by 636 days.

(21) Appl. No.: 12/382,377

(22) Filed: Mar. 16, 2009

(65) Prior Publication Data

US 2010/0233758 A1    Sep. 16, 2010

(51) Int. Cl.
*C07K 14/03*    (2006.01)
*C07K 14/00*    (2006.01)
(52) U.S. Cl. ............. 514/4.2; 514/1.1; 514/3.7; 530/350
(58) Field of Classification Search ......................... None
See application file for complete search history.

(56) References Cited

U.S. PATENT DOCUMENTS 6,291,207 B1 *    9/2001    Spear et al. .................. 435/69.1

OTHER PUBLICATIONS

Asano et al. Efficient construction of a diabody using a refolding system: anti-carcinoembryonic antigen recombinant antibody fragment. J Biochem. Dec. 2002;132(6):903-9.*
Nakano et al. Herpes simplex virus targeting to the EGF receptor by a gD-specific soluble bridging molecule. Mol Ther. Apr. 2005;11(4):617-26.*
Montgomery et al. Herpes simplex virus-1 entry into cells mediated by a novel member of the TNF/NGF receptor family. Cell. Nov. 1, 1996;87(3):427-36.*

* cited by examiner

*Primary Examiner* — Zachariah Lucas
*Assistant Examiner* — Michelle S Horning
(74) *Attorney, Agent, or Firm* — Cantor Colburn LLP

(57) ABSTRACT

Provided are an isolated protein derived from an N-terminal of HveA/HVEM and having activity of increasing the cell infectivity of herpes simplex virus (HSV) and use thereof.

10 Claims, 14 Drawing Sheets

(1 of 14 Drawing Sheet(s) Filed in Color)

PROTEIN INCREASING CELL INFECTIVITY OF HERPES SIMPLEX VIRUS AND USE THEREOF

BACKGROUND OF THE INVENTION

1. Field of the Invention

The present invention relates to an isolated protein increasing a cell infectivity of herpes simplex virus and use thereof.

This work has been supported in part by research grants from Korean Ministry of Education, Science & Technology [Project No.: M1053040003-08N3404-00310, Title: Cancer gene therapy by targeted HSV-1 development. And Project No.: M20702020001-08N0202-00110, Title: Development of combinational radiotherapeutic agents and validation system.]

2. Description of the Related Art

Herpes simplex virus (HSV) which is a DNA virus containing about 150 kb of genome is an enveloped icosahedral virion with a size of about 100 to about 200 nm. HSV enters a cell by attaching glycoprotein B (gB) or glycoprotein C (gC) of its envelope to glycosaminoglycan (GAG) of the surface of the cell, and binding glycoprotein D (gD) of its envelope to various receptors of the surface of the cell to induce fusion of the HSV with membranes of the cell (Spear P G. Cell Microbiol. 2004; 6(5):401-410; Spear P G, Eisenberg R J, Cohen G H. Virology. 2000; 275(1):1-8).

Receptors of the cell surface for HSV include HveA/HVEM, HveC/nectin-1, and HveB/nectin-2 proteins. Herpes virus entry mediator A (HveA/HVEM) is a member of a tumor necrosis factor receptor (TNFR) superfamily and acts as a receptor for HSV-1 and HSV-2 (Whitbeck J C et al., J. Virol. 1997; 71(8): 6083-6093). HveA/HVEM is often expressed in lymphoid tissues such as B-lymphoma or T-lymphoma (Montgomery R I et al., Cell. 1996; 87(3): 427-436). HveA/HVEM is composed of 4 cysteine-rich domains (CRDs).

Gene therapy includes introduction of foreign genes into individuals for the prevention and treatment of diseases. Vectors used for the introduction of the foreign genes include viral vectors or virus-derived vectors. Virus-derived vectors include an adenoviral vector, a retroviral vector, and a herpes simplex viral vector. The adenoviral vector has high gene delivery efficiency and may deliver genes into both proliferating and nonproliferating cells. On the other hand, repeated use of the adenoviral vector may induce strong immunoreactivity, and the size of genes is limited when using the adenoviral vector. The herpes simplex viral vector may deliver relatively large genes and also deliver genes into neural cells.

According to Laquerre S et al., erythropoietin is fused to N-terminal of glycoprotein C of herpes simplex viral surface to obtain erythropoietin-glycoprotein C fusion protein, and HSV containing the erythropoietin-glycoprotein C fusion protein is introduced into cells in which an erythropoietin receptor is expressed. However, since the virus is introduced into cells by an endocytosis instead of by a fusion, the HSV is degraded in the cells, and thus transduction efficiency of the HSV is low. (Laquerre S et al., J. Virol. 1998. December; 72(12): 9683-9697).

SUMMARY OF THE INVENTION

The present invention provides an isolated protein derived from a HveA/HVEM protein and having activity of increasing the cell infectivity of herpes simplex virus (HSV) and its fusion protein.

The present invention also provides a gene encoding the isolated protein.

The present invention also provides an expression vector including the gene.

The present invention also provides a host cell including the gene.

The present invention also provides a method of producing the isolated protein.

BRIEF DESCRIPTION OF THE DRAWINGS

The patent or application file contains at least one drawing executed in color. Copies of this patent or patent application publication with color drawings will be provided by the office upon request and payment of the necessary fee.

The above and other features and advantages of the present invention will become more apparent by describing in detail exemplary embodiments thereof with reference to the attached drawings in which.

DETAILED DESCRIPTION OF THE INVENTION

Figure 1:
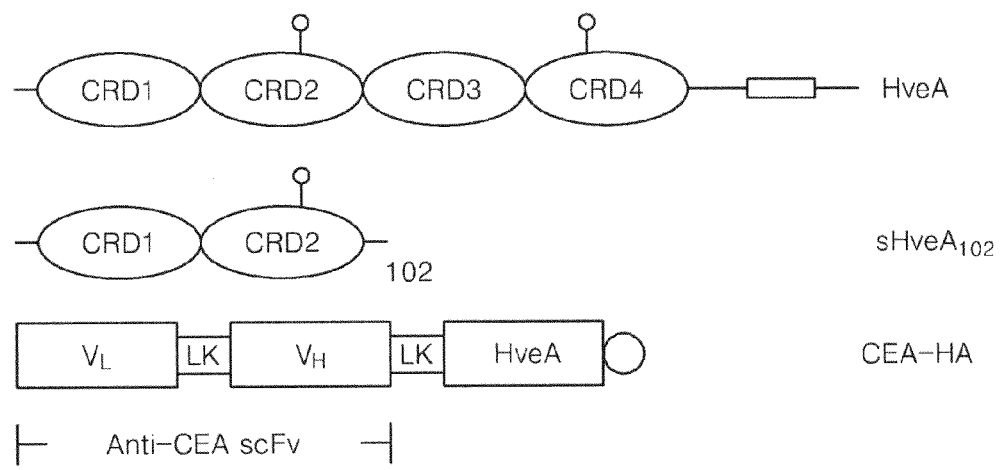
FIG. 1 schematically illustrates constructions of HveA/HVEM, sHveA$_{102}$, anti-CEA scFv-HA$_{82}$ (CEA-HA)

Hereinafter, the present invention will be described more fully with reference to the accompanying drawings, in which exemplary embodiments of the invention are shown.

The present invention provides an isolated protein having activity of increasing the cell infectivity of herpes simplex virus (HSV). The isolated protein may be selected from a group consisting of sHveA$_{82}$ consisting of an amino acid sequence of SEQ ID NO: 12, sHveA$_{87}$ consisting of an amino acid sequence of SEQ ID NO: 14, and sHveA$_{107}$ consisting of an amino acid sequence of SEQ ID NO: 16.

The cell may be a mammalian cell obtained from mammals such as humans, mice, hamsters, monkeys, chimpanzees, cows, pigs, sheep, dogs, and cats. The cell may be a HSV-resistant cell, for example, a CHO-K1 cell. The phrase "HSV-resistant cell" intends to mean a cell resistant to a HSV infection, wherein the HSV is a HSV strain with glycoprotein D capable of binding to its cognate receptors on the host cell surface. The cell may also be a cell cannot be infected by the HSV strain. The protein may be soluble, for example, water-soluble.

The isolated protein may be derived from N-terminal of herpes virus entry mediator A (HveA/HVEM) of HSV-1. Each of the $sHveA_{82}$, $sHveA_{87}$, and $sHveA_{107}$ proteins (sHveA) is a fragment respectively consisting of 82, 87, and 107 amino acids and derived from the N-terminal. The isolated proteins, including a functional analogue of the isolated protein, may have greater cell infectivity of HSV into a HSV-resistant cell line, for example CHO-K1 cell and greater specificity than $sHveA_{102}$. The $sHveA_{102}$ is a fragment consisting of 102 amino acids derived from N-terminal of HveA/HVEM and consisting of an amino acid sequence of SEQ ID NO: 2. The $sHveA_{102}$ may be encoded by a nucleic acid including a base sequence of SEQ ID NO: 1.

The HveA/HVEM may be human HveA/HVEM. The human HveA/HVEM may have an amino acid sequence of SEQ ID NO: 17 and a base sequence of SEQ ID NO: 18 (GeneBank accession No. U70321). The human HveA/HVEM is composed of an N-terminal region existing in the extracellular region, a transmembrane domain, and a C-terminal region existing in the intracellular region. Substitution, addition, or deletion of amino acid may be conducted in the isolated protein to the extent that it does not substantially influence functions of the protein or increase functions of the protein. The isolated protein having such a modification is hereinafter referred as a functional analogue of the isolated protein. The functional analogue of the isolated protein may be an analogue which does not substantially influence or increase the cell infectivity and/or specificity of infection of a HSV compared with the isolated protein. For example, 6 histidine residues may be added to the C-terminal of the protein in order to facilitate the production or isolation of the protein. The functional analogue of the isolated protein may be protein having an analogous amino acid substitution(s) or a conservative amino acid substitution(s) for the amino acids recited in the sequence. It is also to be understood that the isolated protein may either be extended by the addition of further amino acids to either terminus of the sequence, or alternatively that the sequence may be modified by deletion of amino acids from either terminus. As desired, the functional analogue of the isolated protein is also included in the scope of the present invention. For example, the $sHveA_{82}$ gene may further include an additional amino acid sequence of 6 histidines prior to a stop codon. The amino acid sequence of the 6 histidines may be used for the identification of the protein using western blot and the isolation of the protein using a PROBOND nickel-chelating resin, a nickel-charged affinity resin, when expressed as a recombinant protein.

The HSV may be HSV-1 and/or HSV-2. For example, the HSV may be selected from a group consisting of HSV-1 KOS, HSV-1 KOS/tk12, HSV-1 Rid1, and HSV-1 QOZHG. The HSV-1 KOS is wild type HSV-1, HSV-1 KOS/tk12 is prepared by introducing a lacZ gene, as a reporter gene, into a thymidine kinase gene of wild type HSV-1 KOS, HSV-1 Rid1 is mutant HSV-1 from which capability of binding to HveA protein of the cell surface is removed by the mutation of glycoprotein D existing in the virus envelope of wild type HSV-1 KOS. In addition, HSV-1 QOZHG is a replication-incompetent HSV-1 mutant derived from wild type HSV-1 KOS.

The isolated protein may be fused to a fusion partner. The fusion partner may be a protein. An N-terminal or C-terminal of the fusion partner protein may be fused to an N-terminal or C-terminal of the isolated protein. The fusion partner protein may bind to a cell surface substance. The cell surface substance may be a protein, sugar, and/or lipid. The cell surface substance may be specifically expressed by a certain cell type. The cell surface substance may be a substance specifically existing in cancer cells (tumor marker). The tumor marker may be carcinoembryonic antigen (CEA), prostate specific antigen (PSA), and CA15-3. In addition, the cell surface substance may be a growth factor receptor (e.g., EGFR), CD20, or an erythropoietin (EPO) receptor.

The cell surface substance may be a substance specifically expressed in a certain tissue cell. The tissue may be obtained from a nerve, the uterus, breast, lung, liver, prostate, rectum, colon, or thyroid gland. The fusion partner protein binding to the cell surface substance may be a ligand, a receptor, an antibody, or a fragment thereof. The fusion partner protein may be an antibody binding to CEA or a fragment thereof, an antibody binding to an epidermal growth factor receptor (EGFR) or a fragment thereof, an antibody binding to CD20 or a fragment thereof, or an EPO or a fragment thereof.

The fusion protein may be anti-CEA scFv-$HA_{82}$ including an amino acid sequence set of SEQ ID NO: 4. The anti-CEA antibody may be prepared using methods known in the art. For example, the anti-CEA antibody may be prepared by introducing a CEA antigen into a heterologous animal such as a mouse or rabbit, isolating cells producing an anti-CEA antibody, fusing the isolated cells with immortal cells to obtain hybridoma cells, culturing the obtained hybridoma cells, and isolating the anti-CEA antibody from the culture. Genes encoding scFv antibody may be prepared from the anti-CEA antibody using methods known in the art. The genes encoding the scFv antibody may be prepared by identifying genes in heavy and light chain variable regions of the gene sequence of the anti-CEA antibody, amplifying the genes, and ligating the genes in the heavy and light chain variable regions using nucleic acid recombination techniques. A sequence encoding a linker may be contained between the genes in the heavy and light chain variable regions.

The present invention provides a composition comprising the isolated protein and HSV. The HSV may be wild type or recombinant HSV comprising a foreign nucleic acids. The composition may be used for the administration of HSV into a subject body. The subject may be mammal including humans, mice, hamsters, monkeys, chimpanzees, cows, pigs, sheep, dogs, and cats.

The present invention provides a gene encoding the isolated protein. The gene may be a $sHveA_{82}$ gene consisting of a base sequence of SEQ ID NO: 11, a $sHveA_{87}$ gene consisting of a base sequence of SEQ ID NO: 13, or a $sHveA_{107}$ gene consisting of a base sequence of SEQ ID NO: 15. The isolated protein may be fused to a fusion partner. The gene may be an anti-CEA scFv-$HA_{82}$ gene consisting of a base sequence of SEQ ID NO: 3. The sequence corresponding to the anti-CEA scFv antibody gene in the sequence of SEQ ID NO: 3 is composed of heavy and light chain variable regions. The anti-CEA scFv-$HA_{82}$ gene consisting of a base sequence of SEQ ID NO: 3 encodes a fusion protein in which N-terminal 2 CRDs of HveA/HVEM is linked to anti-CEA scFv using a linker consisting of GGGGS sequence (SEQ ID NO:19) as a mediator. Substitution, addition, or deletion of amino acid may be performed in the CEA scFv-$HA_{82}$ protein to the extent that they do not influence functions of the protein.

The isolated protein and the gene encoding the protein may be isolated from human cells or synthesized using known methods of synthesizing DNA or peptides. The gene may also be prepared using known nucleic acid recombination techniques. Furthermore, the prepared gene may be inserted into a vector for microbial expression known in the art to prepare an expression vector, and host cells, e.g., *E. coli* or yeast cells may be transformed with the expression vector. The genes may be replicated or protein may be produced using the transformed host cells. The sHveA protein or fusion protein of sHveA protein and its fusion partner may be prepared by transforming for example, *E. coli* DH5α or CHO cell with a vector containing genes of sHveA protein or fusion protein of sHveA protein and its fusion partner, and culturing the transformed cells for example, *E. coli* DH5α or CHO cell. While preparing the vector, an expression regulatory sequence such as a promoter and a terminator, a self-replicating sequence, and a secretion sequence may be appropriately selected and combined according to the types of the host cell.

The present invention provides an expression vector including a gene encoding the isolated protein. The vector may express the gene in prokaryotic cells or eukaryotic cells. Vectors used in bacteria may include pQE70, pQE60, and pQE-9 (Qiagen); a pBS vector, a PHAGESCRIPT vector, a Bluescript vector, pNH8A, pNH16a, pNH18A, and pNH46A (Stratagene); ptrc99a, pKK223-3, pKK233-3, pDR540, and pRIT5 (Pharmacia), etc. Eukaryotic cell vectors may include pWLNEO, pSV2CAT, pOG44, pXT1, and pSG (Stratagene); and pSVK3, pBPV, pMSG, and pSVL (Pharmacia), etc. The vector may be a pcDNA3.1 vector (Invitrogen) (SEQ ID NO: 20).

The expression vector may be sHveA gene-pcDNA3.1 or sHveA fusion protein gene-pcDNA3.1 in which a sHveA gene or a gene of fusion protein of sHveA and its fusion partner is inserted into HindIII or BamHI and XhoI site of a pcDNA3.1 vector. The vector may be an expression cassette including a cytomegalovirus promoter site, a multiple cloning site, and a late polyadenylation signal site of bovine growth hormone (BGH). The expression vector of pcDNA3.1 vector may be a commercially available vector for mammalian expression. The expression vector may be prepared by inserting a sHveA gene or a gene of fusion protein of sHveA and its fusion partner into a pcDNA3.1 vector using restriction enzymes, etc., and transforming a host cell, e.g., DH5α cell with the pcDNA3.1 vector. The amplification of the sHveA gene or the gene of fusion protein of sHveA and its fusion partner may be performed using known methods, e.g., polymerase chain reaction (PCR). The expression vector of sHveA gene-pcDNA3.1 or sHveA fusion protein gene-pcDNA3.1, which expresses sHveA protein or fusion protein of sHveA and its fusion partner, may be prepared using the sHveA gene or the gene of the fusion protein of sHveA and its fusion partner. The sHveA fusion protein gene-pcDNA3.1 may be anti-CEA scFv-sHveA-pcDNA3.1. The anti-CEA scFv-sHveA-pcDNA3.1 may be anti-CEA scFv-HA$_{82}$-pcDNA3.1. The fusion protein anti-CEA scFv-HA$_{82}$ may be composed of a single-chain variable fragment (scFv) of the anti-CEA antibody and sHveA$_{82}$.

The present invention provides a host cell including the gene. The gene may be introduced into host cells using methods known in the art. The gene may be introduced into host cells using one method selected from a group consisting of using a liposome-mediated gene, electroporation, and bombardment. The gene may be introduced into cells alone or in a construct operatively linked to a regulatory sequence such as a promoter, a replication origin, and a transcription terminator sequences. For example, the gene may be introduced into cells using the expression vector as a vehicle. The host cells into which the gene is introduced may be bacterial cells, yeast cells, or mammalian cells. For example, the host cells may be mammalian cells. The mammalian cells may be 293T cells, HeLa, COS, or CHO. The gene may be inserted into chromosomes of cells or independently exists outside of chromosomes in the cells.

The present invention provides a method of producing the isolated protein, the method including: culturing a host cell containing the gene; and isolating the protein from the culture.

The method includes culturing a host cell containing the gene. The culture of the host cell may be performed using methods known in the art. For example, if the host cell is a 293T cell, the host cell may be cultured in a Dulbecco's modified Eagle's medium (DMEM) supplemented with 10% heat-inactivated fetal bovine serum (FBS) (high glucose+glutamine+sodium pyruvate), or in a DMEM supplemented with 10% heat-inactivated FBS, 200 mM L-glutamine, 10 mM MEM non-essential amino acid, and 100 mM MEM Sodium pyruvate (high glucose+glutamine) under 5 to 7% $CO_2$ conditions.

The method includes isolating the protein from the culture. The isolation may be performed using methods known in the art. The isolation may be performed by lysing cells, and isolating protein from the lysates. The isolation may be performed using a method selected from a group consisting of centrifugation, salting out, ion exchange chromatography, affinity chromatography, hydrophobic chromatography, and size exclusion chromatography.

The present invention provides a method of introducing HSV into cells, the method including contacting HSV with the cells in the presence of the isolated protein. The contact may be performed in vitro or in vivo. The contact may be performed by culturing the HSV and the cells using an appropriate culture medium or buffer. The culture medium may be any medium that is commonly used to culture cells. For example, the culture medium may be a DMEM, or Ham's F12-K, but is not limited thereto. In this case, the cell having an introduced HSV may be administered in a subject body. The subject body may be mammals, for example, a human body. The contact may be performed by administering a composition comprising the HSV and the isolated protein into a subject body. The amount of the composition to be administered may be suitably determined by a person having an ordinary skill in the art. The amount may be therapeutically effective amount. A known method of administering the composition in the art may be used for the method. For example, the method may be selected from the group consisting of liposome tranfection, electroporation, and bombardment. In this case, the HSV may be directly introduced into a cell in the subject. The cell may be a human cell. The HSV may be wild type HSV or a recombinant HSV having a foreign gene. The foreign gene may be selected according to the desired purposes for the introduction of the foreign gene in the host cell. For example, the foreign may be a gene replacing a defective gene, e.g., an intact exogenous gene, or a gene not existing in the cell. Therefore, the method can be applied in the treatment or prevention of diseases in a subject in need of the expression of the foreign gene.

Hereinafter, the present invention will be described more specifically with reference to the following examples. The following examples are for illustrative purposes and are not intended to limit the scope of the present invention.

EXAMPLES

The experiments used to obtain the following comparative examples and examples were performed using methods commonly used in molecular biology.

The methods commonly used in molecular biology, such as plasmid extraction for purification, plasmid DNA centrifugation in a cesium chloride gradient, agarose or acryl amide gel electrophoresis, DNA fragment purification by electroelution, transformation of *E. coli*, etc., are well known in the art and disclosed by Maniatis T. et al., "Molecular Cloning, a Laboratory Manual", Cold Spring Harbor Laboratory, Cold Spring Harbor, N.Y. 1982 (2nd Ed., 1989).

For ligation, DNA fragments were sorted according to their size using agarose or acryl amide gel electrophoresis and treated at a constant temperature in the presence of a phage T4 DNA ligase (Biolabs).

Enzymatic amplification of DNA fragments by PCR was performed using a "DNA thermal cycler" (Perkin Elmer Cetus). The identification of base sequences was performed using a kit (Amersham) and using a method disclosed by Sanger, et al. [Proc. Natl. Acad. Sci. USA, 74 (1977) 5463-5467].

Plasmid DNA was purified using a Qiagen plasmid purification system (Qiagen).

Comparative Example 1

Preparation of Recombinant Expression Vector Expressing sHveA$_{102}$

Figure 2:
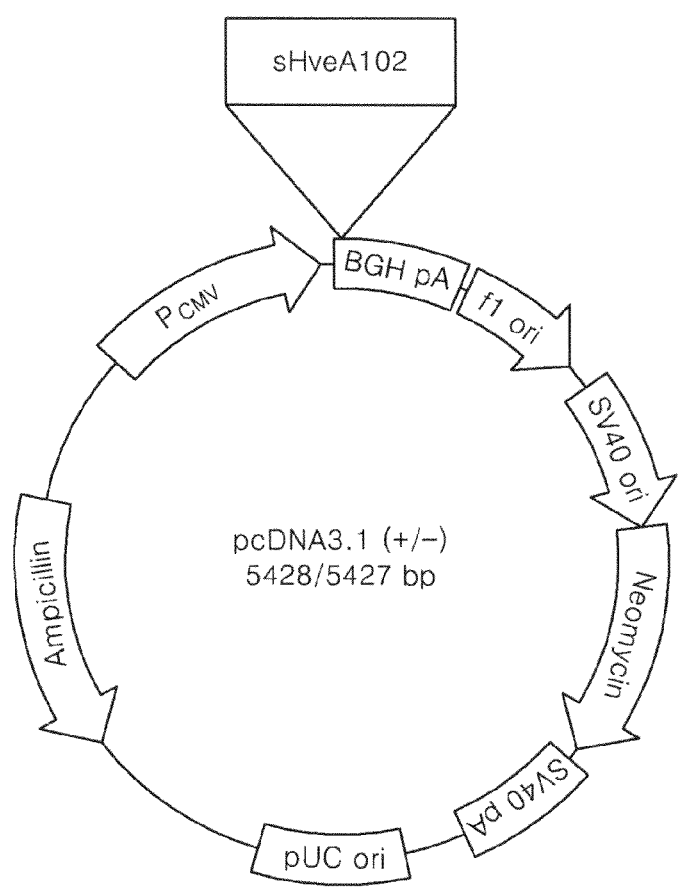
FIG. 2 illustrates sHveA$_{102}$-pcDNA3.1, which is a recombinant protein expression vector.
Figure 3:
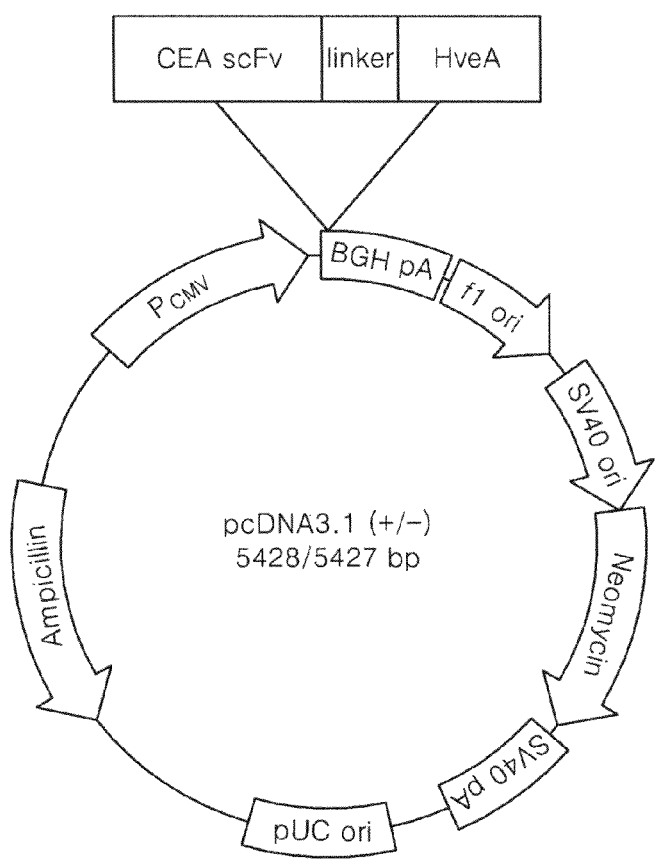
FIG. 3 illustrates anti-CEA scFV-HA$_{82}$-pcDNA3.1, which is a recombinant protein expression vector.

A normal human sHveA$_{102}$ gene was obtained from a human HveA/HVEM gene by PCR using a forward primer (SEQ ID NO: 5) and a reverse primer (SEQ ID NO: 6). The PCR was performed as follows: 0.1 µg of HveA/HVEM DNA, 10 pmol of primers (SEQ ID NOS: 5 and 6, respectively), 10 units of Taq polymerase (Takara), 1× buffer solution, and 2.5 mM dNTP were mixed and water was added thereto such that the volume of the mixture was 50 µl. The sHveA$_{102}$ DNA was amplified by pre-denaturing a template DNA at 95° C. for 5 minutes, performing 30 cycles: at 94° C. for 1 minute, at 60° C. for 1 minute, and at 72° C. for 1 minute, and performing a final extension at 72° C. for 10 minutes. The amplified sHveA$_{102}$ DNA was isolated using column chromatography. The reverse primer (SEQ ID NO: 6) included an amino acid sequence encoding 6 histidines. In order to insert the sHveA$_{102}$ DNA into a multiple cloning site of the pcDNA3.1 vector, the vector and the sHveA$_{102}$ DNA were cleaved using HindIII and XhoI restriction enzymes. The isolated sHveA$_{102}$ DNA was ligated into the vector, and the host cell of DH5α was transformed by the vector. Among them, normal sHveA$_{102}$-pcDNA3.1 was selected and mass-produced. FIG. 1 schematically illustrates constructions of HveA/HVEM and sHveA$_{102}$. FIG. 2 illustrates sHveA$_{102}$-pcDNA3.1, a recombinant protein expression vector.

Comparative Example 2

Figure 4:
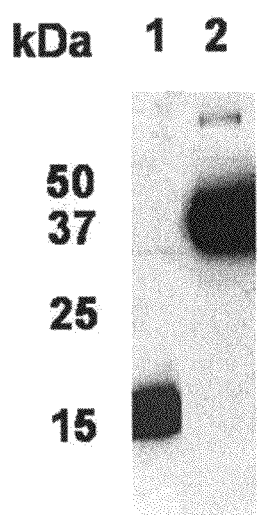
FIG. 4 illustrates expressions of sHveA$_{102}$ (lane 1) and anti-CEA scFv-HA$_{82}$ (lane 2) of culture media including 293T cell lines into which sHveA$_{102}$-pcDNA3.1 plasmid and anti-CEA scFv-HA$_{82}$-pcDNA3.1 plasmid are introduced, which is measured by using western blot.

Expression and Purification of Recombinant sHveA$_{102}$ Protein 293T cells were used in order to produce recombinant sHveA$_{102}$ protein. 15 µg of the mass-produced sHveA$_{102}$-pcDNA3.1 vector was mixed with a culture medium without antibiotics, and 30 µl of lipofectamine was mixed with a culture medium without antibiotics. The two culture media were mixed and treated at room temperature for about 15 minutes so that the vector was introduced into the 293T cells by the mediation of lipofectamine. After the cells were cultured at 37° C. for 5 hours, the culture solution was removed, and then the cells were cultured in a DMEM supplemented with 10% fetal bovine serum (FBS) for 3 days. The culture supernatant was mixed with 1 ml of PROBOND resin (Invitrogen) at 4° C. for 1 hour to bind recombinant sHveA$_{102}$ protein with the PROBOND resin. The reaction solution was passed through a His tag affinity column, and the culture medium unbound to the resin was washed using 20 ml of a phosphate buffer solution containing 10 mM imidazole. Protein bound to the resin was eluted using 5 ml of a phosphate buffer solution containing 250 mM imidazole, and the eluted protein was dialyzed against 1× phosphate-buffered saline (PBS) three times each for 2 hours. The protein obtained by the dialysis was quantified using a Bradford assay, and the expression of the protein was identified using western blot. Lane 1 of FIG. 4 illustrates 500 ng of isolated sHveA$_{102}$ protein. The numbers shown on the left side of the lane are markers indicating the size of the protein. Referring to FIG. 4, sHveA$_{102}$ (lane 1) has the size of 15 kDa.

Comparative Example 3

Cell Infection of HSV by sHveA$_{102}$

It was identified whether the recombinant sHveA$_{102}$ protein efficiently mediates the entry of HSV into HSV-resistant cells.

Figure 5A:
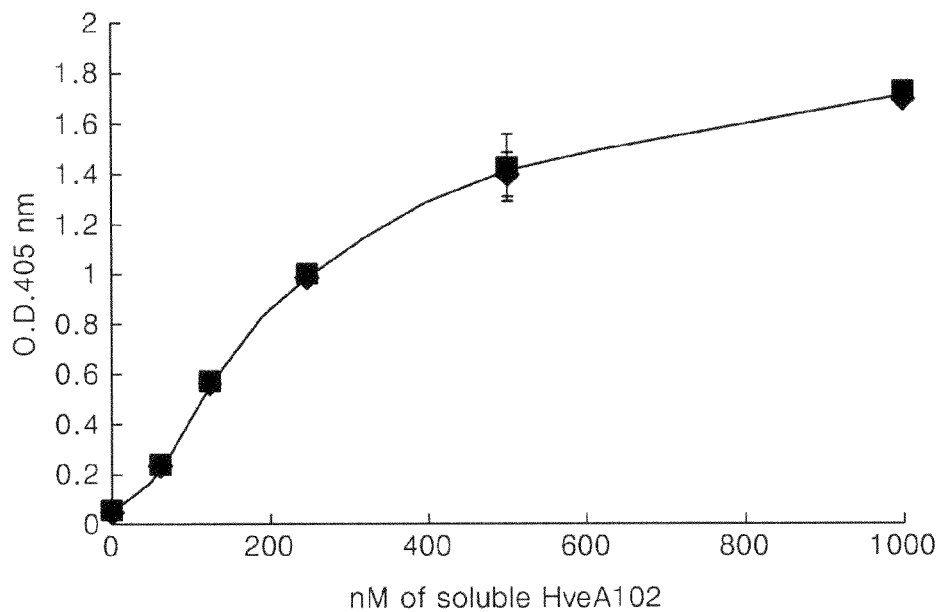
FIGS. 5A and 5B illustrate level of HSV infection into HSV-resistant cell line, CHO-K1, mediated by 0 to 1000 nM recombinant sHveA$_{102}$ protein.
Figure 5B:
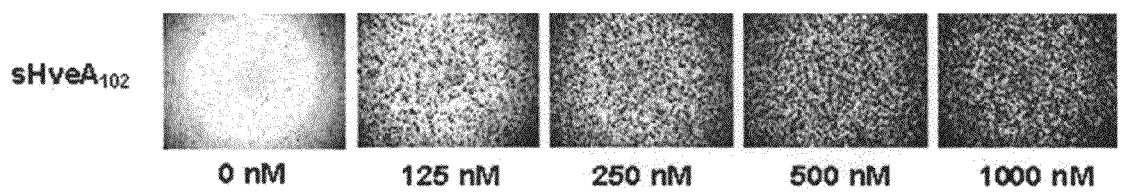
Figure 6A:
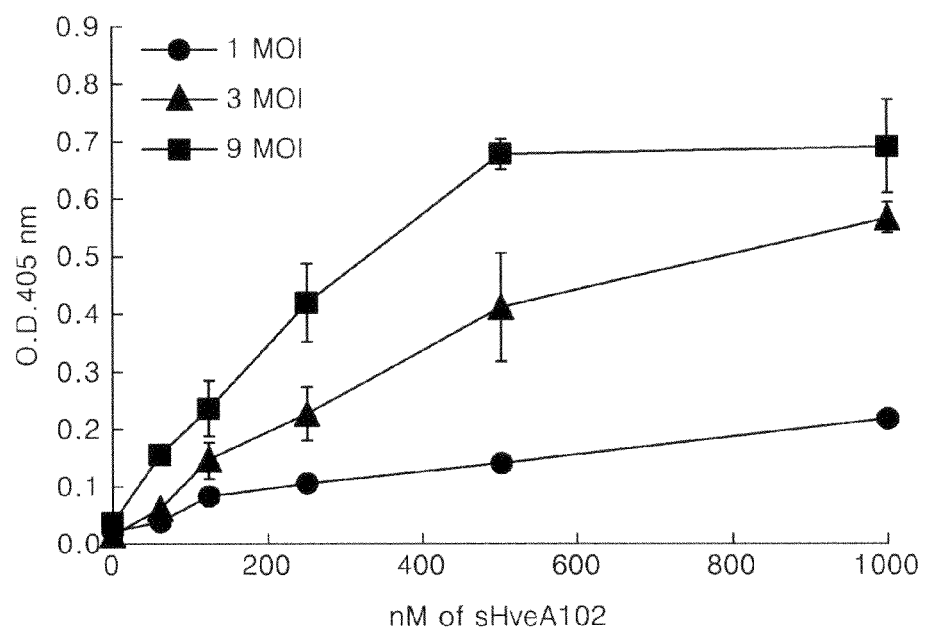
FIGS. 6A and 6B illustrate level of HSV infection according to the number of multiplicity of infection (MOI) and the concentration of recombinant sHveA$_{102}$ protein.
Figure 6B:
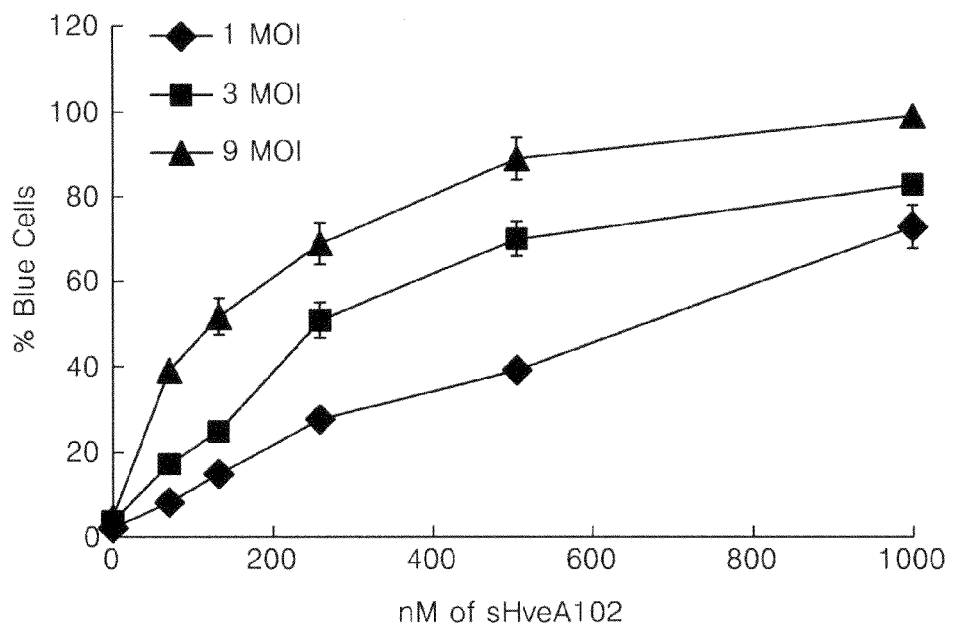

$4.2 \times 10^5$ of a HSV-resistant cell line, CHO-K1, was mixed with HSV-1 KOS/tk12 prepared by introducing a lacZ gene, as a reporter gene, into a thymidine kinase gene of wild type HSV-1 KOS (Dr. Patricia G. Spear, Northwestern University) at a multiplicity of infection (MOI) ranging from 1 to 9, and the mixture was shaking cultured at 4° C. for 1 hour. Each of 0, 62.5, 125, 250, 500, and 1000 nM of sHveA$_{102}$ was diluted in PBS, and the diluted solution was added to a culture medium containing the virus and the cells. They were shaking cultured at 37° C. for 1 hour. 40 µl of each of the resultants were respectively added to wells of a 96-well plate (Corning Inc. NY, USA). The cells were cultured in a Ham's F12-K supplemented with 10% FBS (JRH Biosciences Inc. Kansas, USA), streptomycin, and penicillin G (WeIGENE Inc. Daegu, South Korea) at 37° C. under 5% $CO_2$ conditions and under sufficient moisture conditions. Level of HSV-1 KOS/tk12 infection was measured after 6 to 8 hours of culture using X-gal (5-bromo-4-chloro-3-indolyl β-D-galactopyranoside; Sigma) staining and 2-nitrophenyl-β-galactopyranoside (ONPG; Sigma) assay. Since the reporter gene of LacZ is inserted into the HSV-1 KOS/tk12, β-galactosidase is expressed when a cell is infected with the virus. In the presence of β-galactosidase, X-gal yields a blue color. Thus, the infected cells may be observed using an optical microscope by fixing the cell line infected with HSV-1 KOS/tk12 using 1% glutaraldehyde (Sigma), and reacting the cell line with an X-gal solution. Similarly, ONPG yields a yellow color in the presence of β-galactosidase, and absorbance may be measured. In FIG. 5A, the number on the x-axis indicates the concentration of sHveA$_{102}$, and the number on the y-axis indicates level of virus infection. FIG. 5B illustrates shapes of cells according to the concentration of sHveA$_{102}$. As shown in FIG. 5A, the level of HSV-1 KOS/tk12 infection increased as the concentration of sHveA$_{102}$ increased. As a result of observing the level of the virus infection according to the MOI of the virus and the concentration of sHveA$_{102}$, the level of the virus infection increased as the MOI of the virus increased and as the concentration of sHveA$_{102}$ increased, as shown in FIG. 6A. FIG. 6B is a graph illustrating the percentage of cells infected with the virus, wherein the amount of cells infected is the same as that shown in FIG. 6A by staining the cells using X-gal staining. In general, about 70% of the cells were infected with the virus when 3 MOI of the virus and 500 nM of $sHveA_{102}$ were used.

Comparative Example 4

Specificity of HSV Infection by $sHveA_{102}$

It was identified whether the HSV infection into the HSV-resistant cell by $sHveA_{102}$ shown in Comparative Example 3 is specific to glycoprotein D according to the following process.

Virus infection specificity by $sHveA_{102}$ was measured using HSV-1 KOS/tk12, which is prepared by introducing a lacZ gene, as a reporter gene, into wild type HSV-1 KOS, and HSV-1 Rid1, from which capability of binding to HveA protein of the cell surface is removed by the mutation of glycoprotein D existing in the virus envelope of wild type HSV-1 KOS (Dr. Patricia G. Spear, Northwestern University).

Figure 8:
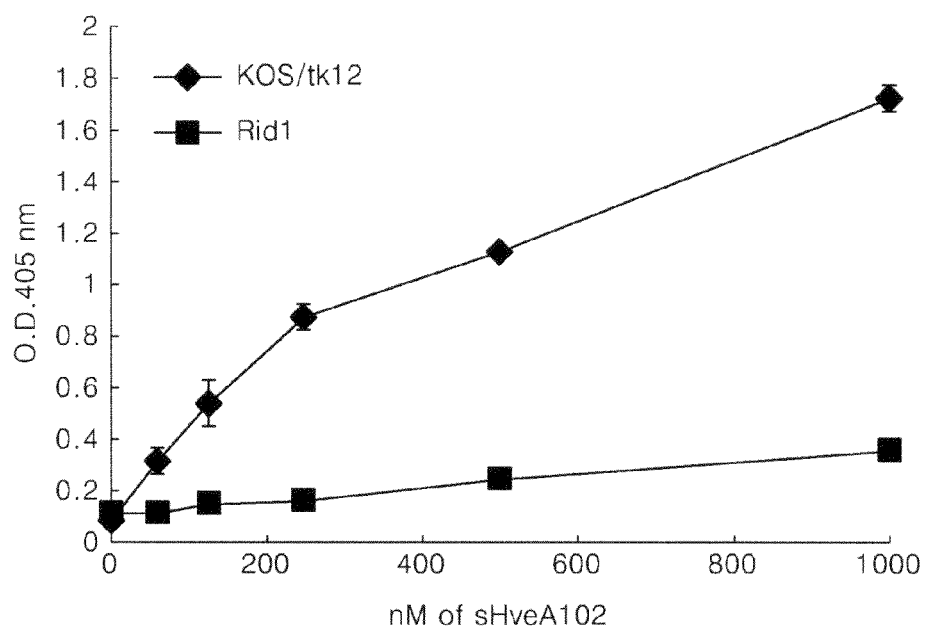
FIG. 8 illustrates level of HSV KOS/tk12 and HSV Rid1 infections into CHO-K1 mediated by recombinant sHveA$_{102}$.

Each of HSV-1 KOS/tk12 and HSV-1 Rid1 was mixed with a CHO-K1 cell line in the same manner as in Comparative Example 3, and 0 to 1000 nM of $sHveA_{102}$ was added thereto. The mixture was treated at 37° C. for 1 hour, and the resultants were respectively added to wells of a 96-well plate. The cells were cultured in a culture medium at 37° C. for 6 to 8 hours under 5% $CO_2$ conditions and under sufficient moisture conditions. The level of the virus infection was measured using X-gal staining and ONPG assay in the same manner as in Comparative Example 3. As shown in FIG. 8, since HSV-1 Rid1 without capability of binding to HveA cannot bind to $sHveA_{102}$, the cells were not infected. On the other hand, cells were more efficiently infected with the wild type virus as the concentration of $sHveA_{102}$ increased.

Example 1

HSV Infection by $sHveA_{82}$ and $sHveA_{107}$

Figure 7A:
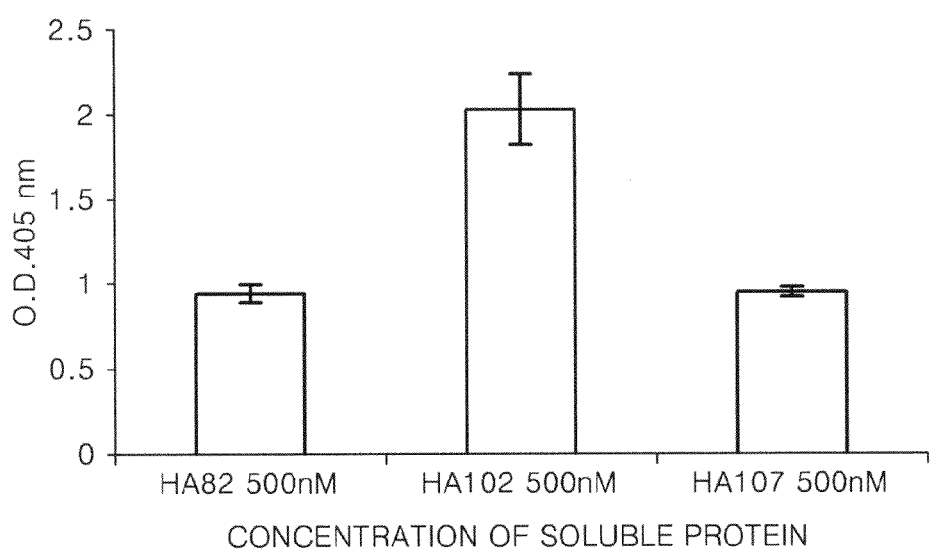
FIGS. 7A and 7B illustrate level of HSV infection into HSV-resistant cell line, CHO-K1, mediated by 500 nM recombinant sHveA protein.
Figure 7B:
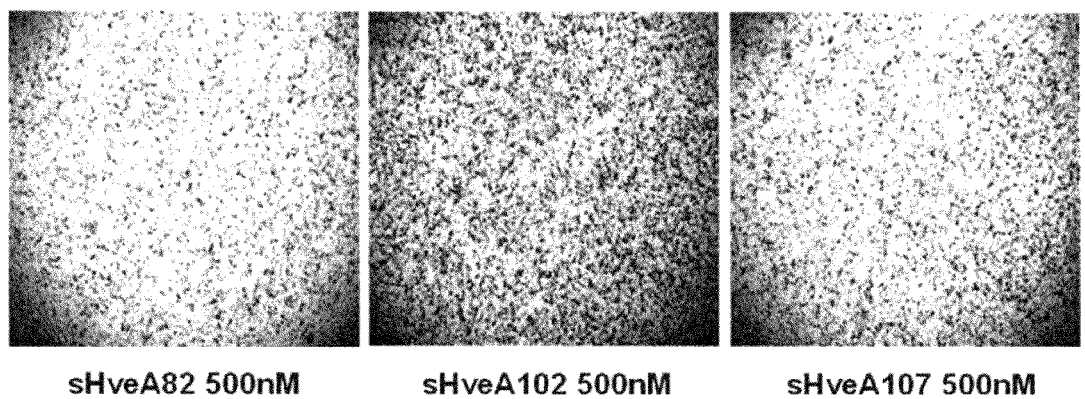

It was identified whether protein efficiently mediates the entry of a virus into HSV-resistant cells, CHO-K1 cells in the same manner as in Comparative Example 3, except that recombinant $sHveA_{82}$ protein and recombinant $sHveA_{107}$ protein were used. In FIG. 7A, the x-axis indicates 500 nM recombinant sHveA proteins, and the number on the y-axis indicates the level of the virus infection. FIG. 7B illustrates infected cells according to the increasing concentrations of sHveA protein.

Example 2

Figure 9:
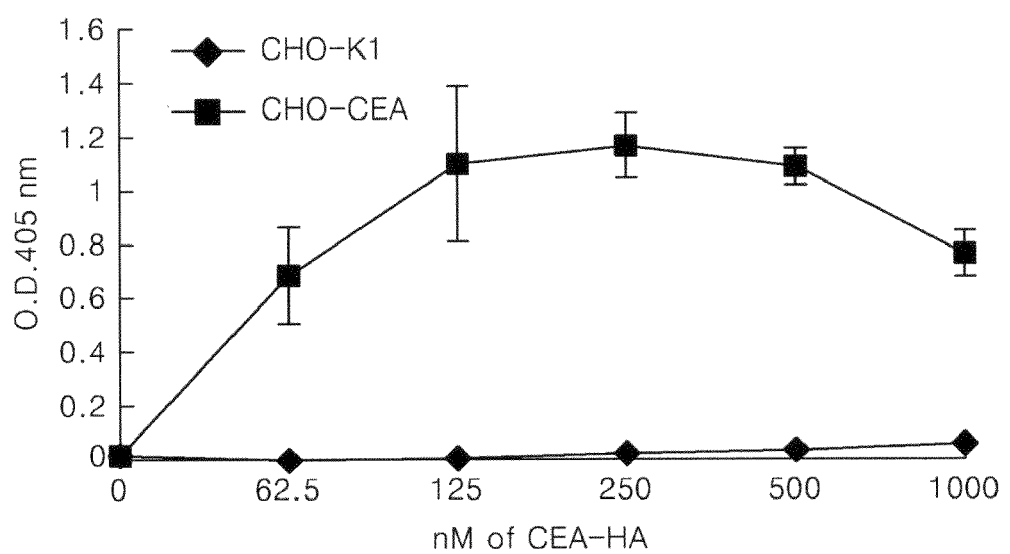
FIG. 9 illustrates level of HSV infection into CHO-K1 and CHO-CEA expressing carcinoembryonic antigen (CEA) mediated by recombinant anti-CEA scFv-HA$_{82}$.

Preparation of Recombinant Expression Vector Expressing Anti-CEA scFv-$HA_{82}$

An anti-CEA scFv gene was obtained by PCR using a forward primer (SEQ ID NO: 7) and a reverse primer (SEQ ID NO: 8), and using a pre-provided anti-CEA scFv gene as a template. The PCR was performed as follows: 0.1 μg of anti-CEA scFv DNA, 10 pmol of primers (SEQ ID NOS: 7 and 8, respectively), 10 units of Taq polymerase (Takara), 1× buffer solution, and 2.5 mM dNTP were mixed and water was added thereto such that the volume of the mixture was 50 μl. The anti-CEA scFv DNA was amplified by pre-denaturing the template DNA at 95° C. for 5 minutes, performing 30 cycles: at 94° C. for 1 minute, at 60° C. for 1 minute, and at 72° C. for 1 minute, and performing a final extension at 72° C. for 10 minutes. The amplified anti-CEA scFv DNA was isolated using column chromatography. The reverse primer (SEQ ID NO: 8) included a base sequence encoding GGGGS amino acid sequence (SEQ ID NO: 19). In order to insert the anti-CEA scFv DNA into a multiple cloning site of the pcDNA3.1 vector, the vector and the anti-CEA scFv DNA were cleaved using BamHI and EcoRI restriction enzymes. The isolated anti-CEA scFv was ligated into the vector, and a host cell of DH5α was transformed by the vector. Among them, normal anti-CEA scFv-pcDNA3.1 was selected and mass-produced.

Then, a $sHveA_{82}$ gene was obtained by PCR using a forward primer (SEQ ID NO: 9) and a reverse primer (SEQ ID NO: 10). The PCR was performed as follows: 0.1 μg of HVEM/HveA DNA, 10 pmol of primers (SEQ ID NOS: 9 and 10, respectively), 10 units of Taq polymerase (Takara), 1× buffer solution, and 2.5 mM dNTP were mixed and water was added thereto such that the volume of the mixture was 50 μl. The $sHveA_{82}$ DNA was amplified by pre-denaturing the template DNA at 95° C. for 5 minutes, performing 30 cycles: at 94° C. for 1 minute, at 60° C. for 1 minute, and at 72° C. for 1 minute, and performing a final extension at 72° C. for 10 minutes. The amplified $sHveA_{82}$ DNA was isolated using column chromatography. The reverse primer (SEQ ID NO: 10) included an amino acid sequence encoding 6 histidines. In order to insert the $sHveA_{82}$ DNA into a multiple cloning site of the anti-CEA scFv-pcDNA3.1 vector, the vector and the $HveA_{82}$ DNA were cleaved using EcoRI and XhoI restriction enzymes. The isolated $HveA_{82}$ was ligated into the vector, and the host cell of DH5α was transformed by the vector. Among them, normal anti-CEA scFv-$HA_{82}$-pcDNA3.1 was selected and mass-produced. FIG. 1 schematically illustrates constructions of anti-CEA scFv-$HA_{82}$. FIG. 3 illustrates anti-CEA scFV-$HA_{82}$-pcDNA3.1, a recombinant protein expression vector.

Example 3

Expression and Purification of Recombinant Anti-CEA scFv-$HA_{82}$ Protein

Expression and purification of the recombinant anti-CEA scFv-$HA_{82}$ protein were performed in the same manner as in Comparative Example 2. As shown in FIG. 4, protein having about 37 kDa of molecular size (lane 2) was isolated and purified.

Example 4

HSV Infection by Anti-CEA scFv-$HA_{82}$

It was identified whether a recombinant anti-CEA scFv-$HA_{82}$ protein efficiently mediates the entry of a virus into HSV-resistant cells expressing CEA (CHO-CEA cell line).

$6\times10^4$ of CHO-K1 and CHO-CEA, which are HSV-resistant cell lines, were added to each well of a 96-well plate, and the cells were cultured in a Ham's F12-K supplemented with 10% FBS, streptomycin, and penicillin G at 37° C. under 5% $CO_2$ conditions and under sufficient moisture conditions. 10 MOI of QOZHG, as HSV-1, was mixed with 0, 62.5, 125, 250, 500, and 1000 nM of anti-CEA scFv-$HA_{82}$ diluted in a PBS, and the mixture was shaking cultured at 4° C. for 1 hour. The QOZHG, as a mutant HSV-1, is a replication-incompetent HSV-1 mutant. 40 μl of each of the reaction solutions were respectively added to wells of a 96-well plate in which CHO-K1 and CHO-CEA were cultured, and the resultant was cultured in a Ham's F12-K supplemented with 10% FBS, streptomycin, and penicillin G at 37° C. under 5% $CO_2$ conditions and under sufficient moisture conditions. After 14 to 16 hours of the culture, the level of QOZHG infection was measured using X-gal staining and ONPG assay. Since the reporter gene of LacZ is inserted into the QOZHG, β-galactosidase is expressed when a cell is infected with the virus. In the presence of β-galactosidase, X-gal yields a blue color. Thus, the QOZHG infected cells may be observed using an optical microscope by fixing a cell line infected with QOZHG using 1% glutaraldehyde (Sigma), and reacting the cell line with an X-gal solution. Similarly, ONPG yields a yellow color in the presence of β-galactosidase, and absorbance may be measured. In FIG. 9, the x-axis indicates the concentration of CEA-HA, and the y-axis indicates the level of the virus infection. As shown in FIG. 9, the level of QOZHG infection increased as the concentration of CEA scFv-$HA_{82}$ increased in the CHO-CEA cell line.

Example 5

Comparison of Effects of Anti-CEA scFv-$sHA_{82}$ and Anti-CEA-scFv-$sHA_{102}$ for HSV Infection Effects of anti-CEA scFv-$sHA_{82}$ and anti-CEA scFv-$sHA_{102}$ for HSV infection were compared with each other.

(1) Preparation of Recombinant Expression Vector Expressing Anti-CEA scFv-$HA_{102}$ A recombinant expression vector which expresses anti-CEA scFv-$HA_{102}$ was prepared using anti-CEA scFv-$HA_{82}$ cloned in a pcDNA 3.1 vector. First, a sHve$A_{102}$ gene was obtained by PCR using a forward primer (SEQ ID NO: 9) and a reverse primer (SEQ ID NO: 10), and using HVEM/HveA DNA as a template. The PCR was performed as follows: 0.1 μg of HVEM/HveA DNA, 10 pmol of forward and reverse primers, 10 units of Taq polymerase (Takara), 1× buffer solution, and 2.5 mM dNTP were mixed and water was added thereto such that the volume of the mixture was 50 μl. The sHve$A_{102}$ DNA was amplified by pre-denaturing the template DNA at 95° C. for 5 minutes, performing 30 cycles: at 94° C. for 1 minute, at 60° C. for 1 minute, and at 72° C. for 1 minute, and performing a final extension at 72° C. for 10 minutes. The amplified sHve$A_{102}$ DNA was isolated using column chromatography. The reverse primer included an amino acid sequence encoding 6 histidines. $HA_{82}$ sites of an anti-CEA scFv-$HA_{82}$-pcDNA3.1 vector were cleaved using EcoRI and XhoI restriction enzymes and removed, and the sHve$A_{102}$ DNA was ligated into the vector using EcoRI and XhoI restriction enzymes. The host cell of E. coli TOP10 (Invitrogen) was transformed by the vector. Among them, normal anti-CEA scFv-$HA_{102}$-pcDNA3.1 was selected and mass-produced.

(2) Expression and Purification of Recombinant Anti-CEA scFv-$HA_{102}$ Protein 293T cells were used in order to produce recombinant anti-CEA scFv-$HA_{102}$ protein. 15 μg of the mass-produced anti-CEA scFv-$HA_{102}$-pcDNA3.1 vector and 15 μl of welfect Enhancer-Q (WeIGENE Inc. Daegu, South Korea) were mixed with a culture medium without antibiotics. The mixture was treated at room temperature for about 15 minutes, and 30 μl of Welfect-Ex (WeIGENE Inc. Daegu, South Korea) was added thereto. The mixture was treated at room temperature for about 15 minutes and added to the 293T cells. After the cells were cultured at 37° C. for 5 hours, the culture solution was removed, and then the cells were cultured in a culture medium supplemented with 10% FBS for 3 days. The culture supernatant was mixed with 1 ml of PROBOND resin (Invitrogen) at 4° C. for 1 hour to bind recombinant CEA scFv-$HA_{102}$ protein with the PROBOND resin. The reaction solution was passed through a column, and the culture medium unbound to the resin was washed using 20 ml of a phosphate buffer solution containing 10 mM imidazole. Protein bound to the resin was eluted using 5 ml of a phosphate buffer solution containing 250 mM imidazole, and the eluted proteins were dialyzed against 1×PBS three times each for 2 hours. The protein obtained by the dialysis was quantified using s Bradford assay, and the expression of the protein was identified using western blot.

(3) HSV Infection by Anti-CEA scFv-$HA_{102}$ and Anti-CEA scFv-$HA_{82}$

Figure 10A:
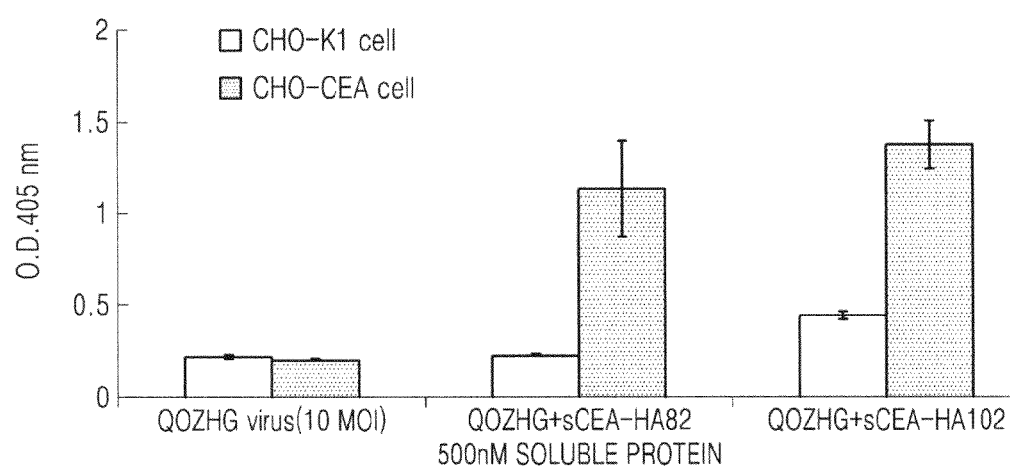
FIGS. 10A and 10B illustrate level of QOZHG virus infection according to the concentration of anti-CEA scFv-HA protein.
Figure 10B:
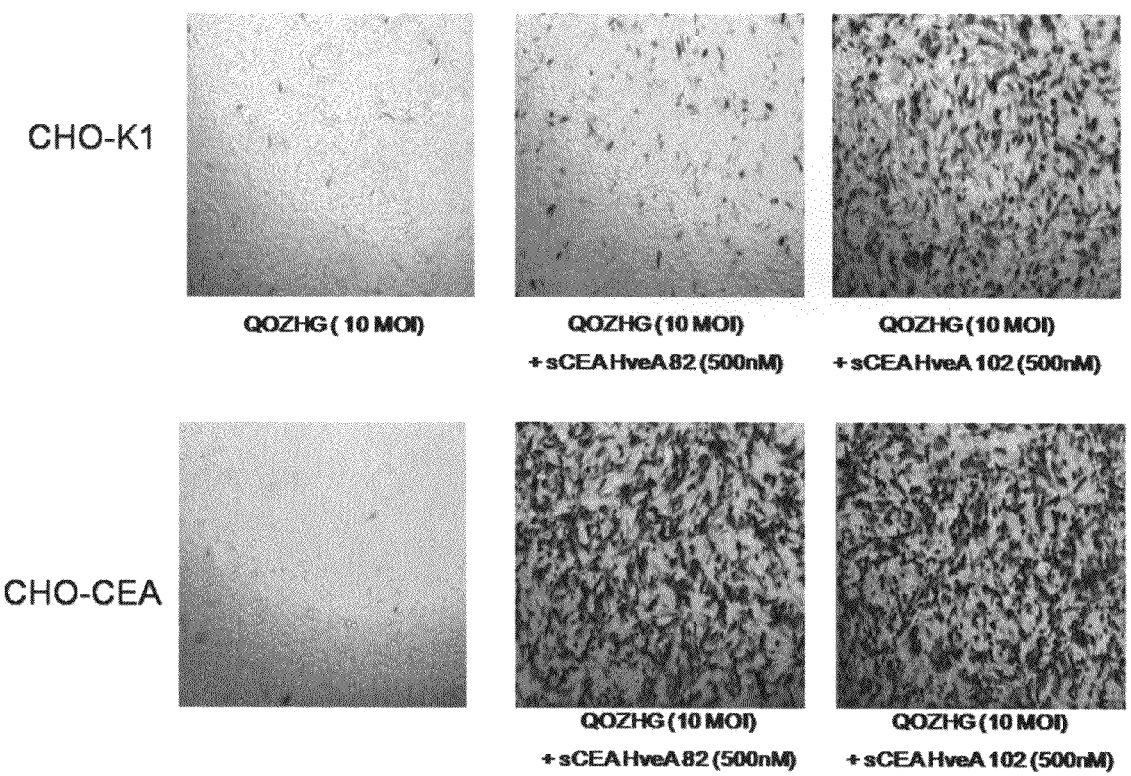

Virus infections by anti-CEA scFv-$HA_{102}$ and anti-CEA scFv-$HA_{82}$ were compared with each other in order to identify whether recombinant CEA scFv-$HA_{102}$ protein efficiently mediates the entry of virus into a CHO-CEA cell line expressing CEA. $6\times10^4$ of CHO-K1 and CHO-CEA, which are HSV-resistant cell lines, were added to each well of a 96-well plate, and the cells were cultured in a Ham's F12-K supplemented with 10% FBS, streptomycin, and penicillin G at 37° C. under 5% $CO_2$ conditions and under sufficient moisture conditions. 10 MOI of QOZHG, as HSV-1, was mixed with each of 500 nM anti-CEA scFv-$HA_{82}$ and anti-CEA scFv-$HA_{102}$ diluted in a PBS and the mixture was shaking cultured at 4° C. for 1 hour. 40 μl of each of the reaction solutions were respectively added to each well of a 96-well plate in which CHO-K1 and CHO-CEA were cultured, and the resultant was cultured in a Ham's F12-K supplemented with 10% FBS, streptomycin, and penicillin G at 37° C. under 5% $CO_2$ conditions and under sufficient moisture conditions. After 14 to 16 hours of the culture, the level of QOZHG infection was measured using X-gal staining and ONPG assay. Since the reporter gene of LacZ is inserted into the QOZHG, β-galactosidase is expressed when a cell is infected with the virus. In the presence of β-galactosidase, X-gal yields a blue color. Thus, the QOZHG infected cells may be observed using an optical microscope by fixing a cell line infected with QOZHG using 1% glutaraldehyde (Sigma), and reacting the cell line with an X-gal solution. Similarly, ONPG yields a yellow color in the presence of β-galactosidase, and absorbance may be measured. In FIG. 10A, the x-axis indicates 500 nM recombinant anti-CEA scFv-HA proteins and QOZHG virus, and the y-axis indicates the level of the virus infection. FIG. 10B illustrates infected cells according to the types of sHveA fusion proteins.

As shown in FIGS. 10A and 10B, when using the recombinant anti-CEA scFv-$HA_{82}$ protein, QOZHG was efficiently infected into only CHO-CEA cells. When using the recombinant anti-CEA scFv-$HA_{102}$ protein, QOZHG was efficiently infected into not only the CHO-CEA cell line but also the CHO-K1 cell line without expressing CEA. This indicates that the anti-CEA scFv-HA102 mediates the entry of HSV-1 into both HSV-resistant cell, CHO-K1 and CHO-K1-CEA, without specificity, however, the anti-CEA scFv-HA82 mediates the entry of HSV-1 into CHO-K1-CEA with high specificity than HSV-resistant cell, CHO-K1. As shown in FIGS. 10A and 10B, the anti-CEA scFv-HA102 mediates the entry of HSV-1 into both HSV-resistant cell, CHO-K1 by 2.5 times more compared with that of anti-CEA scFv-HA82. Thus, the isolated protein may be fused to a partner binding to a cell surface substance to be used to selectively introduce HSV into cells having the substance with high specificity. The HSV may be a HSV having a foreign gene.

According to the present invention, the isolated protein and its fusion protein may be used to mediate the entry of HSV into cells, e.g., HSV-resistant cells. Furthermore, the isolated protein may be efficiently used to mediate the entry of a foreign gene into cells using HSV.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An isolated protein selected from a group consisting of soluble Herpes virus entry mediator A (sHveA)$_{82}$ consisting of an amino acid sequence of positions 1-124 or 1-130 of SEQ ID NO: 12, sHveA$_{87}$ consisting of an amino acid sequence of positions 1-131 or 1-137 of SEQ ID NO: 14, and sHveA$_{107}$ consisting of an amino acid sequence of positions 1-151 or 1-157 of SEQ ID NO: 16.

2. An isolated protein comprising a fragment of soluble Herpes virus entry mediator A (sHveA), fused to a fusion partner which is a protein capable of binding to a cell surface substance, wherein the fragment is selected from the group consisting of sHveA$_{82}$ consisting of an amino acid sequence of positions 1-124 or 1-130 of SEQ ID NO: 12, sHveA$_{87}$ consisting of an amino acid sequence of positions 1-131 or 1-137 of SEQ ID NO: 14, and sHveA$_{107}$ consisting of an amino acid sequence of positions 1-151 or 1-157 of SEQ ID NO: 16.

3. The isolated protein of claim 2, wherein the fusion partner is selected from a group consisting of a ligand, a receptor, and an antibody capable of binding to the cell surface substance, and a fragment thereof.

4. The isolated protein of claim 2, wherein an N-terminal or C-terminal of the fusion partner is fused to an N-terminal or C-terminal of the isolated protein.

5. The isolated protein of claim 2, wherein the fusion partner is selected from a group consisting of an antibody capable of binding to carcinoembryonic antigen (CEA) or a fragment thereof, an antibody capable of binding to an epidermal growth factor receptor (EGFR) or a fragment thereof, an antibody capable of binding to CD20 or a fragment thereof, and an erythropoietin (EPO) or a fragment thereof.

6. The isolated protein of claim 5, which is anti-CEA single chain variable fragment (scFv)-HveA $(HA)_{82}$ consisting of an amino acid sequence of SEQ ID NO: 4.

7. A composition comprising the isolated protein of claim 1 and a herpes simplex virus.

8. A method of introducing herpes simplex virus into a cell, the method comprising contacting herpes simplex virus with the cell in the presence of the isolated protein of claim 1.

9. A method of introducing herpes simplex virus into a cell, the method comprising contacting herpes simplex virus with the cell in the presence of isolated protein of claim 2.

10. The method of claim 9, wherein the cell is a herpes simplex virus-resistant cell.

* * * * *

SEQUENCE LISTING

<160> NUMBER OF SEQ ID NOS: 21

<210> SEQ ID NO 1
<211> LENGTH: 465
<212> TYPE: DNA
<213> ORGANISM: Homo sapiens

<400> SEQUENCE: 1
aagcttgcca ccatggagcc tcctggagac tggggggcctc ctccctggag atccaccccc     60
agaaccgacg tcttgaggct ggtgctgtat ctcaccttcc tgggagcccc ctgctacgcc    120
ccagctctgc cgtcctgcaa ggaggacgag tacccagtgg gctccgagtg ctgccccaag    180
tgcagtccag gttatcgtgt gaaggaggcc tgcggggagc tgacgggcac agtgtgtgaa    240
ccctgccctc caggcaccta cattgcccac ctcaatggcc taagcaagtg tctgcagtgc    300
caaatgtgtg acccagccat gggcctgcgc gcgagccgga actgctccag gacagagaac    360
gccgtgtgtg gctgcagccc aggccacttc tgcatcgtcc aggacgggga ccactgcgcc    420
gcgtgccgcg ctggatccca ccatcaccat caccattagc tcgag                    465

<210> SEQ ID NO 2
<211> LENGTH: 148
<212> TYPE: PRT
<213> ORGANISM: Homo sapiens

<400> SEQUENCE: 2

Met Glu Pro Pro Gly Asp Trp Gly Pro Pro Trp Arg Ser Thr Pro
 1               5                  10                  15
Arg Thr Asp Val Leu Arg Leu Val Leu Tyr Leu Thr Phe Leu Gly Ala
                20                  25                  30
Pro Cys Tyr Ala Pro Ala Leu Pro Ser Cys Lys Glu Asp Glu Tyr Pro
            35                  40                  45
Val Gly Ser Glu Cys Cys Pro Lys Cys Ser Pro Gly Tyr Arg Val Lys
        50                  55                  60
Glu Ala Cys Gly Glu Leu Thr Gly Thr Val Cys Glu Pro Cys Pro Pro
 65                 70                  75                  80
Gly Thr Tyr Ile Ala His Leu Asn Gly Leu Ser Lys Cys Leu Gln Cys
                85                  90                  95
Gln Met Cys Asp Pro Ala Met Gly Leu Arg Ala Ser Arg Asn Cys Ser
            100                 105                 110
Arg Thr Glu Asn Ala Val Cys Gly Cys Ser Pro Gly His Phe Cys Ile
        115                 120                 125
Val Gln Asp Gly Asp His Cys Ala Ala Cys Arg Ala Gly Ser His His
    130                 135                 140
His His His His
145

<210> SEQ ID NO 3
<211> LENGTH: 1077
<212> TYPE: DNA
<213> ORGANISM: Homo sapiens

<400> SEQUENCE: 3
ggatccgcca ccatgagtgt gcccactcag gtcctggggt tgctgctgct gtggcttaca    60
ggtgccagat gtgacatcca gatgactcag tctccagcct cccttttctgc atctgtggga   120
gacactgtca ccatcacatg tcgagcaagt gagaacattt atagttattt agcatggtat   180

-continued

```
cagcagaaac agggaaaatc tcctcagctc ctggtctata atgcaaaggc cttatcagaa    240
ggtgtgccgt caaggttcag tggcagtgga tcaggcacac agtttctct gaggatcaac     300
agcctgcagc ctgaagattt tggggattat tactgtcaac atcattataa ttctccttat    360
acgttcggag gggggaccaa actggaaata aagggctcca cctccgggtc tggtaaatct    420
tccgagggca agggccagat ccagttggtg cagtctggac ctgagctgaa gaagcctgga    480
gagacagtca agatctcctg caaggcttct ggttattcct tcacaaacga tggaataaac    540
tgggtgaagc aggctccagg aaagggtttt aagtacatgg ctggataaa caccatcact     600
ggagagccaa catatactga agacttcaag gggcggtttg ccttctcttt ggaaacctct    660
gccagcactg cctatttgca gatcaacaac ctcaaagatg aggacacggc tacattttc    720
tgtgcaaagg ggactgggac gagcgcttac tggggccaag ggactctggt cactgtctct   780
gctggtggtg gcggttcaga attcctgccg tcctgcaagg aggacgagta cccagtgggc   840
tccgagtgct gccccaagtg cagtccaggt tatcgtgtga aggaggcctg cggggagctg   900
acgggcacag tgtgtgaacc ctgccctcca ggcacctaca ttgcccacct caatggccta   960
agcaagtgtc tgcagtgcca aatgtgtgac ccagccatgg gcctgcgcgc gagccggaac  1020
tgctccagga cagagaacgc cgtgtgtggc caccaccacc accaccacta gctcgag     1077
```

<210> SEQ ID NO 4
<211> LENGTH: 356
<212> TYPE: PRT
<213> ORGANISM: Homo sapiens

<400> SEQUENCE: 4

```
Gly Ser Ala Thr Met Ser Val Pro Thr Gln Val Leu Gly Leu Leu Leu
 1               5                  10                  15

Leu Trp Leu Thr Gly Ala Arg Cys Asp Ile Gln Met Thr Gln Ser Pro
            20                  25                  30

Ala Ser Leu Ser Ala Ser Val Gly Asp Thr Val Thr Ile Thr Cys Arg
        35                  40                  45

Ala Ser Glu Asn Ile Tyr Ser Tyr Leu Ala Trp Tyr Gln Gln Lys Gln
    50                  55                  60

Gly Lys Ser Pro Gln Leu Leu Val Tyr Asn Ala Lys Ala Leu Ser Glu
65                  70                  75                  80

Gly Val Pro Ser Arg Phe Ser Gly Ser Gly Ser Gly Thr Gln Phe Ser
                85                  90                  95

Leu Arg Ile Asn Ser Leu Gln Pro Glu Asp Phe Gly Asp Tyr Tyr Cys
            100                 105                 110

Gln His His Tyr Asn Ser Pro Tyr Thr Phe Gly Gly Gly Thr Lys Leu
        115                 120                 125

Glu Ile Lys Gly Ser Thr Ser Gly Ser Gly Lys Ser Ser Glu Gly Lys
    130                 135                 140

Gly Gln Ile Gln Leu Val Gln Ser Gly Pro Glu Leu Lys Lys Pro Gly
145                 150                 155                 160

Glu Thr Val Lys Ile Ser Cys Lys Ala Ser Gly Tyr Ser Phe Thr Asn
                165                 170                 175

Asp Gly Ile Asn Trp Val Lys Gln Ala Pro Gly Lys Gly Phe Lys Tyr
            180                 185                 190

Met Gly Trp Ile Asn Thr Ile Thr Gly Glu Pro Thr Tyr Thr Glu Asp
        195                 200                 205

Phe Lys Gly Arg Phe Ala Phe Ser Leu Glu Thr Ser Ala Ser Thr Ala
    210                 215                 220
```

```
Tyr Leu Gln Ile Asn Asn Leu Lys Asp Glu Asp Thr Ala Thr Phe Phe
225                 230                 235                 240

Cys Ala Lys Gly Thr Gly Thr Ser Ala Tyr Trp Gly Gln Gly Thr Leu
                245                 250                 255

Val Thr Val Ser Ala Gly Gly Gly Ser Glu Phe Leu Pro Ser Cys
            260                 265                 270

Lys Glu Asp Glu Tyr Pro Val Gly Ser Glu Cys Cys Pro Lys Cys Ser
            275                 280                 285

Pro Gly Tyr Arg Val Lys Glu Ala Cys Gly Glu Leu Thr Gly Thr Val
            290                 295                 300

Cys Glu Pro Cys Pro Pro Gly Thr Tyr Ile Ala His Leu Asn Gly Leu
305                 310                 315                 320

Ser Lys Cys Leu Gln Cys Gln Met Cys Asp Pro Ala Met Gly Leu Arg
                325                 330                 335

Ala Ser Arg Asn Cys Ser Arg Thr Glu Asn Ala Val Cys Gly His His
                340                 345                 350

His His His His
            355

<210> SEQ ID NO 5
<211> LENGTH: 41
<212> TYPE: DNA
<213> ORGANISM: Artificial Sequence
<220> FEATURE:
<223> OTHER INFORMATION: forward primer for sHveA102 gene

<400> SEQUENCE: 5
cccaagcttg ccaccatgga gcctcctgga gactgggggc c                    41

<210> SEQ ID NO 6
<211> LENGTH: 54
<212> TYPE: DNA
<213> ORGANISM: Artificial Sequence
<220> FEATURE:
<223> OTHER INFORMATION: reverse primer for sHveA102 gene

<400> SEQUENCE: 6
agactcgagc taatggtgat ggtgatggtg ggatccagcg cggcacgcgg cgca      54

<210> SEQ ID NO 7
<211> LENGTH: 41
<212> TYPE: DNA
<213> ORGANISM: Artificial Sequence
<220> FEATURE:
<223> OTHER INFORMATION: forward primer for CEA scFv gene

<400> SEQUENCE: 7
caaggatccg ccaccatgag tgtgcccact caggtcctgg g                    41

<210> SEQ ID NO 8
<211> LENGTH: 48
<212> TYPE: DNA
<213> ORGANISM: Artificial Sequence
<220> FEATURE:
<223> OTHER INFORMATION: reverse primer for CEA scFv gene

<400> SEQUENCE: 8
cccgaattct gaaccgccac caccagcaga gacagtgacc agagtccc             48

<210> SEQ ID NO 9
<211> LENGTH: 30
<212> TYPE: DNA
<213> ORGANISM: Artificial Sequence
```

<220> FEATURE:
<223> OTHER INFORMATION: forward primer for sHveA82 gene

<400> SEQUENCE: 9
cccgaattcc tgccgtcctg gaaggaggac                                  30

<210> SEQ ID NO 10
<211> LENGTH: 51
<212> TYPE: DNA
<213> ORGANISM: Artificial Sequence
<220> FEATURE:
<223> OTHER INFORMATION: reverse primer for sHveA82 gene

<400> SEQUENCE: 10
ctagactcga gttagtggtg gtggtggtgg tggccacaca cggcgttctc c          51

<210> SEQ ID NO 11
<211> LENGTH: 399
<212> TYPE: DNA
<213> ORGANISM: Homo sapiens

<400> SEQUENCE: 11
aagcttgcca ccatggagcc tcctggagac tgggggcctc ctccctggag atccacccccc   60 agaaccgacg tcttgaggct ggtgctgtat ctcaccttcc tgggagcccc ctgctacgcc   120
ccagctctgc cgtcctgcaa ggaggacgag tacccagtgg gctccgagtg ctgccccaag   180
tgcagtccag gttatcgtgt gaaggaggcc tgcggggagc tgacgggcac agtgtgtgaa   240
ccctgccctc caggcaccta cattgcccac ctcaatggcc taagcaagtg tctgcagtgc   300
caaatgtgtg acccagccat gggcctgcgc gcgagccgga actgctccag gacagagaac   360
gccgtgtgtg gccaccacca ccaccaccac tagctcgag                        399

<210> SEQ ID NO 12
<211> LENGTH: 130
<212> TYPE: PRT
<213> ORGANISM: Homo sapiens

<400> SEQUENCE: 12

Lys Leu Ala Thr Met Glu Pro Pro Gly Asp Trp Gly Pro Pro Trp
 1               5                  10                  15

Arg Ser Thr Pro Arg Thr Asp Val Leu Arg Leu Val Leu Tyr Leu Thr
                20                  25                  30

Phe Leu Gly Ala Pro Cys Tyr Ala Pro Ala Leu Pro Ser Cys Lys Glu
            35                  40                  45

Asp Glu Tyr Pro Val Gly Ser Glu Cys Cys Pro Lys Cys Ser Pro Gly
 50                  55                  60

Tyr Arg Val Lys Glu Ala Cys Gly Glu Leu Thr Gly Thr Val Cys Glu
 65                  70                  75                  80

Pro Cys Pro Pro Gly Thr Tyr Ile Ala His Leu Asn Gly Leu Ser Lys
                85                  90                  95

Cys Leu Gln Cys Gln Met Cys Asp Pro Ala Met Gly Leu Arg Ala Ser
            100                 105                 110

Arg Asn Cys Ser Arg Thr Glu Asn Ala Val Cys Gly His His His His
        115                 120                 125

His His
    130

<210> SEQ ID NO 13
<211> LENGTH: 420
<212> TYPE: DNA

-continued

<213> ORGANISM: Homo sapiens

<400> SEQUENCE: 13

```
aagcttgcca ccatggagcc tcctggagac tgggggcctc ctccctggag atccacccccc    60
agaaccgacg tcttgaggct ggtgctgtat ctcaccttcc tgggagcccc ctgctacgcc   120
ccagctctgc cgtcctgcaa ggaggacgag tacccagtgg gctccgagtg ctgccccaag   180
tgcagtccag gttatcgtgt gaaggaggcc tgcggggagc tgacgggcac agtgtgtgaa   240
ccctgccctc caggcaccta cattgcccac ctcaatggcc taagcaagtg tctgcagtgc   300
caaatgtgtg acccagccat gggcctgcgc gcgagccgga actgctccag gacagagaac   360
gccgtgtgtg gctgcagccc aggccacgga tcccaccatc accatcacca ttagctcgag   420
```

<210> SEQ ID NO 14
<211> LENGTH: 137
<212> TYPE: PRT
<213> ORGANISM: Homo sapiens

<400> SEQUENCE: 14

```
Lys Leu Ala Thr Met Glu Pro Pro Gly Asp Trp Gly Pro Pro Trp
 1               5                  10                  15

Arg Ser Thr Pro Arg Thr Asp Val Leu Arg Leu Val Leu Tyr Leu Thr
            20                  25                  30

Phe Leu Gly Ala Pro Cys Tyr Ala Pro Ala Leu Pro Ser Cys Lys Glu
        35                  40                  45

Asp Glu Tyr Pro Val Gly Ser Glu Cys Cys Pro Lys Cys Ser Pro Gly
    50                  55                  60

Tyr Arg Val Lys Glu Ala Cys Gly Glu Leu Thr Gly Thr Val Cys Glu
65                  70                  75                  80

Pro Cys Pro Pro Gly Thr Tyr Ile Ala His Leu Asn Gly Leu Ser Lys
                85                  90                  95

Cys Leu Gln Cys Gln Met Cys Asp Pro Ala Met Gly Leu Arg Ala Ser
            100                 105                 110

Arg Asn Cys Ser Arg Thr Glu Asn Ala Val Cys Gly Cys Ser Pro Gly
        115                 120                 125

His Gly Ser His His His His His His
    130                 135
```

<210> SEQ ID NO 15
<211> LENGTH: 480
<212> TYPE: DNA
<213> ORGANISM: Homo sapiens

<400> SEQUENCE: 15

```
aagcttgcca ccatggagcc tcctggagac tgggggcctc ctccctggag atccacccccc    60
agaaccgacg tcttgaggct ggtgctgtat ctcaccttcc tgggagcccc ctgctacgcc   120
ccagctctgc cgtcctgcaa ggaggacgag tacccagtgg gctccgagtg ctgccccaag   180
tgcagtccag gttatcgtgt gaaggaggcc tgcggggagc tgacgggcac agtgtgtgaa   240
ccctgccctc caggcaccta cattgcccac ctcaatggcc taagcaagtg tctgcagtgc   300
caaatgtgtg acccagccat gggcctgcgc gcgagccgga actgctccag gacagagaac   360
gccgtgtgtg gctgcagccc aggccacttc tgcatcgtcc aggacgggga ccactgcgcc   420
gcgtgccgcg cttacgccac ctccagcgga tcccaccatc accatcacca ttagctcgag   480
```

<210> SEQ ID NO 16
<211> LENGTH: 157

<212> TYPE: PRT
<213> ORGANISM: Homo sapiens

<400> SEQUENCE: 16

```
Lys Leu Ala Thr Met Glu Pro Pro Gly Asp Trp Gly Pro Pro Trp
1               5                   10                  15

Arg Ser Thr Pro Arg Thr Asp Val Leu Arg Leu Val Leu Tyr Leu Thr
                20                  25                  30

Phe Leu Gly Ala Pro Cys Tyr Ala Pro Ala Leu Pro Ser Cys Lys Glu
            35                  40                  45

Asp Glu Tyr Pro Val Gly Ser Glu Cys Cys Pro Lys Cys Ser Pro Gly
        50                  55                  60

Tyr Arg Val Lys Glu Ala Cys Gly Glu Leu Thr Gly Thr Val Cys Glu
65                  70                  75                  80

Pro Cys Pro Pro Gly Thr Tyr Ile Ala His Leu Asn Gly Leu Ser Lys
                85                  90                  95

Cys Leu Gln Cys Gln Met Cys Asp Pro Ala Met Gly Leu Arg Ala Ser
            100                 105                 110

Arg Asn Cys Ser Arg Thr Glu Asn Ala Val Cys Gly Cys Ser Pro Gly
        115                 120                 125

His Phe Cys Ile Val Gln Asp Gly Asp His Cys Ala Ala Cys Arg Ala
    130                 135                 140

Tyr Ala Thr Ser Ser Gly Ser His His His His His His
145                 150                 155
```

<210> SEQ ID NO 17
<211> LENGTH: 283
<212> TYPE: PRT
<213> ORGANISM: Homo sapiens

<400> SEQUENCE: 17

```
Met Glu Pro Pro Gly Asp Trp Gly Pro Pro Trp Arg Ser Thr Pro
1               5                   10                  15

Arg Thr Asp Val Leu Arg Leu Val Leu Tyr Leu Thr Phe Leu Gly Ala
                20                  25                  30

Pro Cys Tyr Ala Pro Ala Leu Pro Ser Cys Lys Glu Asp Glu Tyr Pro
            35                  40                  45

Val Gly Ser Glu Cys Cys Pro Lys Cys Ser Pro Gly Tyr Arg Val Lys
        50                  55                  60

Glu Ala Cys Gly Glu Leu Thr Gly Thr Val Cys Glu Pro Cys Pro Pro
65                  70                  75                  80

Gly Thr Tyr Ile Ala His Leu Asn Gly Leu Ser Lys Cys Leu Gln Cys
                85                  90                  95

Gln Met Cys Asp Pro Ala Met Gly Leu Arg Ala Ser Arg Asn Cys Ser
            100                 105                 110

Arg Thr Glu Asn Ala Val Cys Gly Cys Ser Pro Gly His Phe Cys Ile
        115                 120                 125

Val Gln Asp Gly Asp His Cys Ala Ala Cys Arg Ala Tyr Ala Thr Ser
    130                 135                 140

Ser Pro Gly Gln Arg Val Gln Lys Gly Gly Thr Glu Ser Gln Asp Thr
145                 150                 155                 160

Leu Cys Gln Asn Cys Pro Pro Gly Thr Phe Ser Pro Asn Gly Thr Leu
                165                 170                 175

Glu Glu Cys Gln His Gln Thr Lys Cys Ser Trp Leu Val Thr Lys Ala
            180                 185                 190

Gly Ala Gly Thr Ser Ser Ser His Trp Val Trp Trp Phe Leu Ser Gly
```

```
              195                 200                 205
Ser Leu Val Ile Val Ile Val Cys Ser Thr Val Gly Leu Ile Ile Cys
    210                 215                 220

Val Lys Arg Arg Lys Pro Arg Gly Asp Val Val Lys Val Ile Val Ser
225                 230                 235                 240

Val Gln Arg Lys Arg Gln Glu Ala Glu Gly Glu Ala Thr Val Ile Glu
                245                 250                 255

Ala Leu Gln Ala Pro Pro Asp Val Thr Thr Val Ala Val Glu Glu Thr
                260                 265                 270

Ile Pro Ser Phe Thr Gly Arg Ser Pro Asn His
                275                 280

<210> SEQ ID NO 18
<211> LENGTH: 1724
<212> TYPE: DNA
<213> ORGANISM: Homo sapiens

<400> SEQUENCE: 18
ccttcatacc ggcccttccc ctcggctttg cctggacagc tcctgcctcc cgcagggccc     60
acctgtgtcc cccagcgccg ctccacccag caggcctgag cccctctctg ctgccagaca    120
cccccctgctg cccactctcc tgctgctcgg gttctgaggc acagcttgtc acaccgaggc   180
ggattctctt tctcttttctc ttctggccca cagccgcagc aatggcgctg agttcctctg    240
ctggagttca tcctgctagc tgggttcccg agctgccggt ctgagcctga ggcatggagc    300
ctcctggaga ctgggggcct cctccctgga gatccacccc cagaaccgac gtcttgaggc    360
tggtgctgta tctcaccttc ctgggagccc cctgctacgc cccagctctg ccgtcctgca    420
aggaggacga gtacccagtg ggctccgagt gctgccccaa gtgcagtcca ggttatcgtg    480
tgaaggaggc ctgcggggag ctgacgggca cagtgtgtga accctgccct ccaggcacct    540
acattgccca cctcaatggc ctaagcaagt gtctgcagtg ccaaatgtgt gacccagcca    600
tgggcctgcg cgcgagccgg aactgctcca ggacagagaa cgccgtgtgt ggctgcagcc    660
caggccactt ctgcatcgtc caggacgggg accactgcgc cgcgtgccgc gcttacgcca    720
cctccagccc gggccagagg gtgcagaagg gaggcaccga gagtcaggac accctgtgtc    780
agaactgccc cccgggggacc ttctctccca atgggaccct ggaggaatgt cagcaccaga    840
ccaagtgcag ctggctggtg acgaaggccg gagctgggac cagcagctcc cactgggtat    900
ggtggtttct ctcagggagc ctcgtcatcg tcattgtttg ctccacagtt ggcctaatca    960
tatgtgtgaa aagaagaaag ccaaggggtg atgtagtcaa ggtgatcgtc tccgtccagc   1020
ggaaaagaca ggaggcagaa ggtgaggcca cagtcattga ggccctgcag gcccctccgg   1080
acgtcaccac ggtggccgtg gaggagacaa taccctcatt cacggggagg agcccaaacc   1140
actgacccac agactctgca ccccgacgcc agagatacct ggagcgacgg ctgctgaaag   1200
aggctgtcca cctggcgaaa ccaccggagc ccggaggctt gggggctccg ccctgggctg   1260
gcttccgtct cctccagtgg agggagaggt ggggcccctg ctggggtaga gctgggacg    1320
ccacgtgcca ttcccatggg ccagtgaggg cctgggcct ctgttctgct gtggcctgag    1380
ctccccagag tcctgaggag gagcgccagt tgcccctcgc tcacagacca cacacccagc   1440
cctcctgggc cagcccagag ggcccttcag acccagctct ctgcgcgtc tgactcttgt    1500
ggcctcagca ggacaggccc cgggcactgc ctcacagcca aggctggact gggttggctg   1560
cagtgtggtg tttagtggat accacatcgg aagtgatttt ctaaattgga tttgaattcc   1620
ggtcctgtct tctatttgtc atgaaacagt gtatttgggg agatgctgtg ggaggatgta   1680
```

```
aatatcttgt ttctcctcaa aaaaaaaaaa aaaaaaaaaa aaaa            1724
```

<210> SEQ ID NO 19
<211> LENGTH: 5
<212> TYPE: PRT
<213> ORGANISM: Artificial Sequence
<220> FEATURE:
<223> OTHER INFORMATION: Linker

<400> SEQUENCE: 19

Gly Gly Gly Gly Ser
 1               5

<210> SEQ ID NO 20
<211> LENGTH: 5427
<212> TYPE: DNA
<213> ORGANISM: Artificial Sequence
<220> FEATURE:
<223> OTHER INFORMATION: pcDNA3.1(-) Sequence

<400> SEQUENCE: 20

```
gacggatcgg gagatctccc gatcccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaacgg gccctctaga ctcgagcggc cgccactgtg ctggatatct gcagaattcc    960
accacactgg actagtggat ccgagctcgg taccaagctt aagtttaaac cgctgatcag   1020
cctcgactgt gccttctagt tgccagccat ctgttgtttg cccctccccc gtgccttcct   1080
tgaccctgga aggtgccact cccactgtcc tttcctaata aaatgaggaa attgcatcgc   1140
attgtctgag taggtgtcat tctattctgg ggggtgggggt ggggcaggac agcaagggggg   1200
aggattggga agacaatagc aggcatgctg gggatgcggt gggctctatg gcttctgagg   1260
cggaaagaac cagctggggc tctagggggt atccccacgc gccctgtagc ggcgcattaa   1320
gcgcggcggg tgtggtggtt acgcgcagcg tgaccgctac acttgccagc gccctagcgc   1380
ccgctccttt cgctttcttc ccttcctttc tcgccacgtt cgccggcttt ccccgtcaag   1440
ctctaaatcg ggggctccct ttagggttcc gatttagtgc tttacggcac ctcgacccca   1500
aaaaacttga ttagggtgat ggttcacgta gtgggccatc gccctgatag acggtttttc   1560
gccctttgac gttggagtcc acgttcttta atagtggact cttgttccaa actggaacaa   1620
```

```
cactcaaccc tatctcggtc tattcttttg atttataagg gattttgccg atttcggcct    1680
attggttaaa aaatgagctg atttaacaaa aatttaacgc gaattaattc tgtggaatgt    1740
gtgtcagtta gggtgtggaa agtccccagg ctccccagca ggcagaagta tgcaaagcat    1800
gcatctcaat tagtcagcaa ccaggtgtgg aaagtcccca ggctcccccag caggcagaag    1860 tatgcaaagc atgcatctca attagtcagc aaccatagtc ccgcccctaa ctccgcccat    1920
cccgccccta actccgccca gttccgccca ttctccgccc catggctgac taattttttt    1980
tatttatgca gaggccgagg ccgcctctgc ctctgagcta ttccagaagt agtgaggagg    2040
cttttttgga ggcctaggct tttgcaaaaa gctcccggga gcttgtatat ccattttcgg    2100
atctgatcaa gagacaggat gaggatcgtt tcgcatgatt gaacaagatg gattgcacgc    2160
aggttctccg gccgcttggg tggagaggct attcggctat gactgggcac aacagacaat    2220
cggctgctct gatgccgccg tgttccggct gtcagcgcag gggcgcccgg ttcttttttgt    2280 caagaccgac ctgtccggtg ccctgaatga actgcaggac gaggcagcgc ggctatcgtg    2340
gctggccacg acgggcgttc cttgcgcagc tgtgctcgac gttgtcactg aagcgggaag    2400
ggactggctg ctattgggcg aagtgccggg gcaggatctc ctgtcatctc accttgctcc    2460
tgccgagaaa gtatccatca tggctgatgc aatgcggcgg ctgcatacgc ttgatccggc    2520
tacctgccca ttcgaccacc aagcgaaaca tcgcatcgag cgagcacgta ctcggatgga    2580
agccggtctt gtcgatcagg atgatctgga cgaagagcat caggggctcg cgccagccga    2640
actgttcgcc aggctcaagg cgcgcatgcc cgacggcgag gatctcgtcg tgacccatgg    2700
cgatgcctgc ttgccgaata tcatggtgga aaatggccgc ttttctggat tcatcgactg    2760
tggccggctg ggtgtggcgg accgctatca ggacatagcg ttggctaccc gtgatattgc    2820
tgaagagctt ggcggcgaat gggctgaccg cttcctcgtg ctttacggta tcgccgctcc    2880
cgattcgcag cgcatcgcct tctatcgcct tcttgacgag ttcttctgag cgggactctg    2940
gggttcgaaa tgaccgacca agcgacgccc aacctgccat cacgagattt cgattccacc    3000
gccgccttct atgaaaggtt gggcttcgga atcgttttcc gggacgccgg ctggatgatc    3060
ctccagcgcg gggatctcat gctggagttc ttcgcccacc ccaacttgtt tattgcagct    3120
tataatggtt acaaataaag caatagcatc acaaatttca caaataaagc atttttttca    3180
ctgcattcta gttgtggttt gtccaaactc atcaatgtat cttatcatgt ctgtataccg    3240
tcgacctcta gctagagctt ggcgtaatca tggtcatagc tgtttcctgt gtgaaattgt    3300
tatccgctca caattccaca acatacga gccggaagca taaagtgtaa agcctggggt    3360
gcctaatgag tgagctaact cacattaatt gcgttgcgct cactgcccgc tttccagtcg    3420
ggaaacctgt cgtgccagct gcattaatga atcggccaac gcgcggggag aggcggtttg    3480
cgtattgggc gctcttccgc ttcctcgctc actgactcgc tgcgctcggt cgttcggctg    3540
cggcgagcgg tatcagctca ctcaaaggcg gtaatacggt tatccacaga atcaggggat    3600
aacgcaggaa agaacatgtg agcaaaaggc cagcaaaagg ccaggaaccg taaaaaggcc    3660
gcgttgctgg cgttttttcca taggctccgc cccctgacg agcatcacaa aaatcgacgc    3720
tcaagtcaga ggtggcgaaa cccgacagga ctataaagat accaggcgtt tccccctgga    3780
agctccctcg tgcgctctcc tgttccgacc ctgccgctta ccggatacct gtccgccttt    3840
ctcccttcgg gaagcgtggc gctttctcat agctcacgct gtaggtatct cagttcggtg    3900
taggtcgttc gctccaagct gggctgtgtg cacgaaccccc cgttcagccc gaccgctgc    3960 gccttatccg gtaactatcg tcttgagtcc aacccggtaa gacacgactt atcgccactg    4020
```

-continued

```
gcagcagcca ctggtaacag gattagcaga gcgaggtatg taggcggtgc tacagagttc  4080
ttgaagtggt ggcctaacta cggctacact agaagaacag tatttggtat ctgcgctctg  4140
ctgaagccag ttaccttcgg aaaaagagtt ggtagctctt gatccggcaa acaaaccacc  4200
gctggtagcg gtttttttgt ttgcaagcag cagattacgc gcagaaaaaa aggatctcaa  4260
gaagatcctt tgatctttc tacggggtct gacgctcagt ggaacgaaaa ctcacgttaa  4320
gggattttgg tcatgagatt atcaaaaagg atcttcacct agatcctttt aaattaaaaa  4380
tgaagtttta aatcaatcta agtatatat gagtaaactt ggtctgacag ttaccaatgc  4440
ttaatcagtg aggcacctat ctcagcgatc tgtctatttc gttcatccat agttgcctga  4500
ctccccgtcg tgtagataac tacgatacgg gagggcttac catctggccc cagtgctgca  4560
atgataccgc gagacccacg ctcaccggct ccagatttat cagcaataaa ccagccagcc  4620
ggaagggccg agcgcagaag tggtcctgca actttatccg cctccatcca gtctattaat  4680
tgttgccggg aagctagagt aagtagttcg ccagttaata gtttgcgcaa cgttgttgcc  4740
attgctacag gcatcgtggt gtcacgctcg tcgtttggta tggcttcatt cagctccggt  4800
tcccaacgat caaggcgagt tacatgatcc cccatgttgt gcaaaaaagc ggttagctcc  4860
ttcggtcctc cgatcgttgt cagaagtaag ttggccgcag tgttatcact catggttatg  4920
gcagcactgc ataattctct tactgtcatg ccatccgtaa gatgcttttc tgtgactggt  4980
gagtactcaa ccaagtcatt ctgagaatag tgtatgcggc gaccgagttg ctcttgcccg  5040
gcgtcaatac gggataatac cgcgccacat agcagaactt taaaagtgct catcattgga  5100
aaacgttctt cggggcgaaa actctcaagg atcttaccgc tgttgagatc cagttcgatg  5160
taacccactc gtgcacccaa ctgatcttca gcatctttta ctttcaccag cgtttctggg  5220
tgagcaaaaa caggaaggca aaatgccgca aaaaagggaa taagggcgac acggaaatgt  5280
tgaatactca tactcttcct ttttcaatat tattgaagca tttatcaggg ttattgtctc  5340
atgagcggat acatatttga atgtatttag aaaaataaac aaataggggt tccgcgcaca  5400
tttccccgaa aagtgccacc tgacgtc                                      5427

<210> SEQ ID NO 21
<211> LENGTH: 45
<212> TYPE: DNA
<213> ORGANISM: Artificial Sequence
<220> FEATURE:
<223> OTHER INFORMATION: reverse primer

<400> SEQUENCE: 21
cccctcgagg tggtggtggt ggtggtgagc gcggcacgcg gcgca                   45
```